(12) United States Patent
Grezes Besset et al.

(10) Patent No.: US 10,238,044 B2
(45) Date of Patent: Mar. 26, 2019

(54) PLANT BIOTIC AGENT PHENOTYPING PLATFORM AND PROCESS OF PHENOTYPING

(71) Applicant: BIOGEMMA, Paris (FR)

(72) Inventors: Bruno Grezes Besset, Cornebarrieu (FR); Pierre George, Levignac (FR); Jean-Luc Porqueras, Fonsorbes (FR)

(73) Assignee: BIOGEMMA, Paris (FR)

( * ) Notice: Subject to any disclaimer, the term of this patent is extended or adjusted under 35 U.S.C. 154(b) by 0 days.

(21) Appl. No.: 15/037,272

(22) PCT Filed: Nov. 20, 2014

(86) PCT No.: PCT/EP2014/075174
§ 371 (c)(1),
(2) Date: May 17, 2016

(87) PCT Pub. No.: WO2015/075131
PCT Pub. Date: May 28, 2015

(65) Prior Publication Data
US 2016/0278302 A1   Sep. 29, 2016

(30) Foreign Application Priority Data

Nov. 20, 2013 (EP) .................................. 13306587

(51) Int. Cl.
*A01G 9/029* (2018.01)
*A01G 7/00* (2006.01)
(Continued)

(52) U.S. Cl.
CPC .............. *A01G 9/0297* (2018.02); *A01G 7/00* (2013.01); *A01G 7/045* (2013.01); *A01G 9/20* (2013.01);
(Continued)

(58) Field of Classification Search
CPC ....... A01G 9/1066; Y02P 60/216; A01H 9/00; C12M 1/00
See application file for complete search history.

(56) References Cited

U.S. PATENT DOCUMENTS 4,884,366 A * 12/1989 Morton .................. A01G 31/02
47/62 C
2006/0207172 A1   9/2006 McDonald et al.
2011/0010991 A1   1/2011 Fujii et al.

FOREIGN PATENT DOCUMENTS

EP   0052264   *   5/1982   ............. A01G 31/02
EP   0142989       5/1985
(Continued)

OTHER PUBLICATIONS

Fernandez-Martinez et al, Progress in Research on Breeding for Resistance to Sunflower Broomrape, 2012, Hellia, 35, 47-56 (Year: 2012).*

(Continued)

*Primary Examiner* — Narayan K Bhat
(74) *Attorney, Agent, or Firm* — B. Aaron Schulman, Esq.; Stites & Harbison, PLLC

(57) ABSTRACT

The present invention relates to a plant biotic agent phenotyping platform comprising a container hermetically sealed with a lid delimiting an internal space divided into two spaces: -a lower internal space which comprises at least one temperature control means immersed in a temperature transfer liquid; and -an upper internal space, the surface of the temperature transfer liquid being the border between the lower internal space and the upper internal space; the lid comprising at least one orifice which is adapted to fit a pot and at least one pot whose bottom part is contained in the upper internal space and which is adapted to receive plant seeds and soil parasite and to enable development of such soil parasites and plants. The invention also related to the use
(Continued)

of this platform for screening plant resistance or tolerance to soil parasite.

18 Claims, 5 Drawing Sheets

(51) Int. Cl.
    *A01G 31/02*     (2006.01)
    *A01G 7/04*     (2006.01)
    *A01G 9/20*     (2006.01)
    *A01G 9/24*     (2006.01)
    *A01G 25/02*     (2006.01)
    *C12Q 1/6895*     (2018.01)

(52) U.S. Cl.
    CPC .............. *A01G 9/245* (2013.01); *A01G 9/247* (2013.01); *A01G 25/02* (2013.01); *A01G 31/02* (2013.01); *C12Q 1/6895* (2013.01); *C12Q 2600/13* (2013.01); *Y02P 60/216* (2015.11)

(56) References Cited

FOREIGN PATENT DOCUMENTS

| GB | 2217165 | * | 10/1989 |
|---|---|---|---|
| WO | WO 2005/055700 | * | 6/2005 |

OTHER PUBLICATIONS

Written Opinion of the International Searching Authority for PCT/EP2014/075174 dated Jan. 21, 2015.
International Search Report for PCT/EP2014/075174 dated Jan. 21, 2015.
Partial European Search Report completed May 7, 2014.

* cited by examiner

PLANT BIOTIC AGENT PHENOTYPING PLATFORM AND PROCESS OF PHENOTYPING

The present invention relates to a plant biotic agent phenotyping platform, especially a phenotyping platform to soil parasites for example root parasites, plant parasites (*Orobanche*), fungus, nematode, symbiotic organisms. This platform can be used to determine the interaction (for example resistance, tolerance . . . ) between a plant and a soil parasite. For example, this platform can be used to determine sunflower plants resistant or tolerant to different races of *Orobanche*.

*Orobanche* (Broomrape or broom-rape) are parasitic herbaceous plants free of chlorophyll. These plants entirely depend on host-plant for the nutritive elements they need. After germination, *Orobanche* seeds give small roots which fix on the host plant roots and retrieve water and nutritive elements from said host-plant. These plants are named holoparasitic plants. More specifically, *Orobanche Cumana Wallr* (sunflower *Orobanche*) parasitizes roots and causes severe damages to sunflower (Romania, Bulgaria, Turkey, Spain, Ukraine, Russia, Serbia, Hungary and France). There exist different races of *Orobanche Cumana Wallr* according to their location. An internal survey has revealed that 60% of European acreage (8.5 million ha) is infested by *Orobanche Cumana Wallr* from race E to G (mainly in Ukraine and Russia) with yield loss between 10 and 100%. In addition to decrease in yield, *Orobanche* is also responsible of a loss of quality of the plant.

There is thus a need to develop different variety of plants (especially variety of sunflower plants) which can resist to or tolerate different races of *Orobanche*.

Sunflower selection for *Orobanche* resistance or tolerance makes use of different methods for testing breeding materials for example field trial. However, this method is not reliable since there is no control of the inoculum (the phenotyping is only based on the seeds naturally present in the field) and there are variations due to outdoor cultivation (environmental influence such as wind, rain, temperature . . . ). The phenotyping is thus not carried out for a specific race of parasite but for the parasites encountered in the field.

There is thus a need to provide a device and a method for studying and determining the interaction between different plants and different races of soil parasites.

The objective of the present invention is to provide a plant biotic agent phenotyping platform which enables to obtain rapid and reliable determination of interactions between different plants and different soil parasites.

Another objective of the invention is to provide a phenotyping tool that allows controlled, precised and homogeneous growing conditions for any kind of root-soil interaction study: for example interaction between plants and parasite for example: plant parasite, nematode, fungi or bacterial parasite but also to determine the interaction between plant and fungi or bacterial symbiotic organisms.

Another objective of the elements is also to provide a method enabling a rapid and reliable determination of the interaction between different plants and different races of soil parasite for example determination of different sunflower plants resistance or tolerance to different races of *Orobanche*.

A further objective of the present invention is also to provide such method which enables to predict the behavior of plants in field.

An objective of the present invention is to provide quick screen of new variability in order to find new plant resistance sources for evolving races of soil parasite.

A further objective of the invention is also to provide a phenotyping platform which enables to determine races of plant parasite for their aggressiveness. An objective is also to use this method to retrieve, after cultivation DNA and/or RNA of the *Orobanche* in order to carry out genotyping of different races of *Orobanche*.

A last objective of the invention is to use this platform with controlled soil moisture and soil and aerial temperature for plant phenotypical characterization: drought, high and low temperature.

Other objectives of the invention will appear by reading the description of the invention which follows.

The present invention relates to a plant biotic agent phenotyping platform comprising a container hermetically sealed with a lid delimiting an internal space divided into two spaces:
- a lower internal space which comprises at least one temperature control means immersed in a temperature transfer liquid; and
- an upper internal space, the surface of the temperature transfer liquid being the border between the lower internal space and the upper internal space;

the lid comprising at least one orifice which is adapted to fit a pot and at least one pot whose bottom part is contained in the upper internal space and which is adapted to receive plant seed and soil parasite, preferably on soil, and to enable growth of plant seed and development of such soil parasites.

Advantageously, the presence of a pot enables plant root contamination within the pot with the inoculum of soil parasite. Moreover, it enables to confine the roots during plant growing avoiding contamination between the roots of different plants placed into different pots of the platform. Contamination would results in non-reliable results as what is obtained in case of field trial phenotyping. The contamination could be for example the contamination of the roots of a plant of one pot comprising a specific soil parasite with a different soil parasite comprised in another pot.

Preferably, the pot has a size such that when it is in placed within the orifice the pot has a predetermined volume within the upper internal space and the depth of the pot and the volume of temperature transfer liquid are adapted so that the pot is never in contact with the temperature transfer liquid. Preferably, the level of temperature transfer liquid is situated at least at 1 cm of the lower part of the pot, preferably between 1 and 4 cm.

Preferably, the pot has a diameter such as when it is placed within the orifice it fits the diameter of the orifice in order the internal space inside the container being hermetic.

Preferably, the pot is in the form of tube and has a diameter comprised between 2 and 10 cm, preferably between 4 and 6 cm and a length comprised between 3 and 20 cm, preferably comprised between 5 and 15 cm. It is advantageous to use pot in form of tube in order to facilitate the growth of the roots. Typically this does not disrupt the development of the roots of the plant and enables to observe the whole root system. One can use a transparent tube for example to observe the whole root system. The volume of the tube is preferably adapted to the root growth during the test.

Preferably, the platform of the invention comprises n number of orifices, n being comprised between 1 and 1000, preferably between 50 and 500 and m number of pots, m being comprised between 1 and n. When m is lower than n, the platform further comprises closing members in order to close any orifice wherein no plot is placed. The closing members have a size which fits the orifice in order to hermetically close the orifices. The platform can also comprise the same number of orifices and pots and the unused pots are sealed with closing members. Preferably only one type of plant seeds is sowed per pot and only one type of soil parasite is inoculated per pot. It is thus possible with the platform of the invention to study the interaction of n plants with respect to the same soil parasite or of n soil parasites with respect to the same plant or of 1 to n plant(s) with respect to 1 to n soil parasite(s).

Preferably, the pots are in thermic conducting material for example in plastic, polystyrene, polyvinylchloride (PVC), polyethylene or polyethylene high density (PHED).

The pot of the invention is adapted to comprise a nutrient substrate preferably comprising peat, for example sphagnum peat, especially blonde sphagnum peat and fertilizer, for example NPK fertilizer.

Preferably, in the platform of the invention, at least one of the pot comprises a nutrient substrate, preferably as defined above.

Preferably, in the platform of the invention, the pots comprise a soil parasite seed or inoculum placed on the nutrient substrate.

According to the present invention, soil parasite means any parasite which can have interaction with roots of plants. Preferably, the soil parasite is chosen among plant root parasite and can be a plant for example Orobanche, especially Orobanche Cumana Wallr; but also fungus, nematode, basteria or a symbiotic organism preferably chosen among mycorrhiza (for instance Gigaspora rosea), plant growth promoting rhizobacteria (for instance Azospirillum brasilense). The plant parasite can be chosen amongorobanche (for instance Orobanche ramose, Orobanche ramosa, Orobanche aegyptica, Orobanche Cumana Wallr or Orobanche cernua), Sriga (for instance Striga hermonthica, Striga hermonthica or Striga hermonthica), nematodes (for instance meloidogyne), soil-borne fungus (for instance Verticilium dahlia, rhyzoptomia or Plasmodiaphora brassicae.

If the soil parasite is a plant parasite, seeds of this plant parasite are sowed in the pot. If the soil parasite is a symbiotic organism, fungus, nematodes or bacteria, a corresponding inoculum can be directly placed into the pot before the sowing of the plant seed or later after the sowing at any predetermined development stage of the plant.

Preferably, the pot can also comprise host plant seeds one would like to determine the interaction with the soil parasite. The host plant can be chosen among monocotyledons or dicotyledonous plant as sunflower, rapeseed, maize, wheat, rice, sorghum, arabidopsis, pea, tomato.

In one embodiment the soil parasite is a root parasite and is preferably Orobanche, especially Orobanche Cumana Wallr and the host plant is sunflower or rapeseed, preferably sunflower.

The platform according to the invention for example enables to determine the level of interaction between different plants and different races of soil parasite. In case the soil parasite is for example Orobanche, the level of interaction corresponds to the tolerance or the resistance of the plants to different races of Orobanche. It is thus necessary to control homogeneous conditions of the internal space (the conditions into the container) and more particularly of the upper internal space at the vicinity of the pot and in the pot in order to promote the growth of the plant and the development of the soil parasite. By conditions it means especially the temperature of the upper internal space. The conditions at the vicinity of the pot and in the pot is controlled, homogeneous and maintained at the temperature which enables promotion of the development of plants and soil parasites thanks to the temperature control system and the temperature transfer liquid. These controlled conditions can also be achieved by the reduced diameter of the pot which allows temperature transfers into the pot and so homogeneity of the temperature condition within the pot. The temperature control system can be a heating control system or a cooling control system as it is desired to cool the upper internal space or to heat the upper internal space according to the ambient temperature and the optimum temperature for the development of the root parasite. The temperature inside the container can be controlled between 5 and 60° C., for example between 20 and 45° C. For example, if the soil parasite is Orobanche the temperature in the upper internal space and in the pot is comprised between 26 and 30° C., preferably between 27 and 28° C. In order to control temperature, thermometers are placed in the pots and optionally in the upper internal space.

The temperature control system can comprise a thermostat.

The heating system is for example chosen among the one typically used in this field and preferably the heating control system is an electric blanket.

The cooling system is for example chosen among the one typically used in this field and for example it is composed of a tube network filed with a liquid vector for example a mixture of water and glycol which is cooled by an external unit.

In a specific embodiment, the temperature control system is a heating control system and is for example an electric blanket.

The temperature transfer liquid can be any liquid which enables convection of temperature. The temperature transfer liquid is a non-phytotoxic liquid, and is preferably water. The temperature control system is immersed in the temperature transfer liquid and thus enables the formation of a specific atmosphere in the upper space of the container either water vapor in case of heating control mean (like a "bain marie") or cooled atmosphere in case of a cooling control mean. For example, when the temperature control system is a heat control system and the temperature transfer liquid is water, the heating of the water creates water vapor around the pot which is homogeneous inside the upper space of the container and controlled. The level of temperature transfer liquid in the platform can be controlled for example thanks to a translucent tube placed at the end of the platform.

With the platform of the invention all the conditions (temperature, irrigation, plants and soil parasites, etc.) implemented are controlled, and there are no imponderables due to environment (changes of temperatures, irrigation, etc.).

Preferably, the moisture inside the pots is also controlled and optimized according to the nature and origin of the seed and to the soil parasite in order to optimize their interaction and to adapt the platform to all the pathosystems Control of drought or moisture can be done by the use of dispositive to control soil moisture. For examples Capacitance probes are randomly positioned on the platform, and joined to irrigation means to trigger controlled irrigation when the moisture down under a predetermined value, for example moisture in the soil can be controlled for a value between 5 and 25%.

The specific and optimized controlled conditions of the upper space of the container and the architecture of the platform and the pots (reduced size) enable to use a reduced amount of soil parasite compare to other known protocol. These specific and optimized controlled conditions also enable to consider a great number of plants and soil parasite and to adapt to the optimal conditions for each soil parasite development. This system allows rapid identification of plant having low interaction or being tolerant to a soil parasite since the test is carried out on early plant development stage. The platform used small pots and used few quantities of seeds reducing the cost of each tests. The reduced quantity of substrate into each pot allows easier decontamination protocols.

Preferably, the container is made of aluminum, polyvinylchloride, polypropylene, polyethylene, polystyrene, preferably aluminum or polyvinylchloride.

Advantageously, the container also comprises an insulating material which can be placed above the temperature control system or between the temperature control system and the inner surface of the container. Preferably, the insulating material is placed between the temperature control system and the inner surface of the container in order to prevent deterioration of the inner surface of the container and injuries of people using the platform due to low or high temperature. For example the insulating material can be an aqua napping.

Preferably, the container is 1 to 3 m length and 50 cm to 1 m width.

The platform of the invention can further comprise, above the container, irrigation means for example consisting of a drip system delivering a controlled and equal amount of water independently to each pot. This advantageously ensures homogeneous condition of culture, conservation of substrate texture intended to be put into the pot and preservation of the impact of temperature on the substrate. This drip system of the invention is preferably composed of at least one tube network into which the water flows in two opposite directions which join in the central part of the network. The tube network also comprises various jets, advantageously, there is as much as jets than pots and the jets are placed just in front of each pot. This specifically enables to homogeneously split the pressure into the network. Consequently, the difference between the distance between the entry of the network and the closest jet and between the entry of the network and the farthest jet is as low as possible. The difference of irrigation between each pot is thus reduced.

The use of such a drip system enables to provide the essential quantity of water to the plant and soil parasite without cooling effect of the pot. Preferably, the watering is implemented once or twice a week, especially once a week, during between 20 seconds to 4 minutes. The skilled person can determine the optimum conditions of watering with respect to the plant and the soil parasite implemented.

Preferably, the irrigation means for one platform is composed of 2 to 10 different ramp of irrigation means as defined above. This enables to be able to turn on only the ramp in front of the pots used and also to avoid any pressure loss and ensure an homogeneous watering of the different pots.

Preferably, the irrigation system comprises taps feeding each ramp of the system in order to water only the pots used.

Advantageously, the bottom of pots is perforated and filed with for example a cotton balls in order to evacuate the excessive amount of water caused by the irrigation without loss of the substrate.

Advantageously, the elements constituting the platform can be easily decontaminated (decontamination with respect of plant seeds and soil parasite). The lid, the container, the temperature control means and the pot can be washed with chlorinated water, for example Javel water.

The liquid trash (for example the temperature transfer liquid) can be heated between 50 to 150° C. The solid trash (for example the substrate and the operator's clothing) can be autoclaved.

This enables one to ensure the respect of the norms in greenhouse implementing such soil parasites.

Accordingly, the platform of the invention can further comprise at least one temperature transfer liquid decontamination means. Indeed, the temperature transfer liquid can be contaminated by soil parasites or plant seeds when the bottom of the pots is perforated and excess water, due to irrigation, is evacuated into the container. The decontamination is advantageously makes by heating the temperature transfer liquid at a temperature comprised between 50 and 150° C. according to soil parasite resistance to temperature and the temperature transfer liquid used. For example when the soil parasite is Orobanche and the temperature transfer liquid is water, the decontamination is made by heating at a temperature comprised between 70 and 90° C., for example at 80° C., especially between 30 min and 2 h. Thus the decontamination means are any means adapted to heat a predetermined volume of a temperature transfer liquid.

The platform of the invention can further comprise at least one mean for decontamination of the elements constituting the platform (lid, container, temperature control means, pots, etc.). This means can be any means adapted to contain chlorinated water, for example Javel water.

The platform can also comprise at least one mean for decontaminating solid trash for example the substrate or operator's clothing after use of the platform. This mean can be for example an autoclave.

The platform can also comprise lightning means for lightening the pots. The lightning means can be chosen among the one typically used in farming, for example sodium vapor lights.

The present invention also relates to a kit comprising the phenotyping platform as described above, and at least one irrigation means as described above and/or lightning means for lightening the pots and/or decontamination mean(s) as described above.

The present invention also relates to a phenotyping greenhouse comprising one or more phenotyping platform as described above, at least one irrigation means as described above and/or lightning means for lightening the pots and/or decontamination means as described above and/or means for controlling the temperature and the hygrometry inside the greenhouse for example with a fog system. Preferably, the hygrometry inside the greenhouse is comprised between 40 and 60%. Preferably, the temperature inside the greenhouse is comprised between 10 and 40° C., for example between 18 and 22° C.

The greenhouse can further comprise an airlock optionally with a footbath and/or a dressing area with for example a sticky carpet in order to trap any soil parasite in order to warrant controlled conditions and prevent contamination at the vicinity of the platform.

The operator's clothing can be treated with the solid trash and decontaminate by autoclaving.

The present invention also relates to the use of the platform as described above or of the greenhouse as described above for the screening and phenotyping of plants.

The present inventions also relates to a method of identification of the level of interaction between different plants and different races of soil parasite comprising the step of:

Sowing a plant seed on a substrate containing a standard quantity of soil parasite in at least one pot of a phenotyping platform according to the invention and;

Cultivating the plant;
Recovering the plant after a predetermined duration of culture which depends on the development cycle of said soil parasite;
Note the roots and/or aerial damage on the plant.

Advantageously, the method of the invention enables to obtain results in the early development of the plants. This enables to retrieve rapid, homogeneous and repeatable results and to have a rapid screening compared to what is obtained during field trial.

The method of the invention and the use of the platform of the invention enable to obtain results which are correlated with results obtained during field trial. Accordingly, the method of the invention advantageously makes it possible to predict the tolerance or resistance of a plant to a soil parasite and to predict the plants having the lowest interactions with different races of soil parasite.

Advantageously, in the methods of the invention, there are in each pot of the platform one different race of soil parasite and the same plant or one different plant and the same soil parasite or one different race of soil parasite and one different plants.

The soil parasite and the plant (host plant) are as defined above.

The system soil parasite/plant which can be studied are for example chosen among *Gigaspora rosea* and sunflower, rhizobacteria (for instance *Azospirillum brasilense* or *Pseudomonas putida*) and plants; *Orobanche ramosa* and *Arabidopsis thaliana*, *Orobanche ramosa* and *Brassica napus*, *Orobanche aegyptica* and *Arabidopsis thaliana* or *Orobanche cernua* and pea, *Striga hermonthica* and Maize, *Striga hermonthica* and Rice or *Striga hermonthica* and sorghum, meloidogyne and maize, sorghum or tomato, *Verticilium dahlia* on sunflower, rhyzoptomia on *Brassica napus* or plasmodiaphora Brassicae on *Brassica napus*.

Preferably, in the methods of the invention, after recovering of the roots and before noting the roots and/or aerial damage on the plants, the roots are washed with water. The decontamination of the water issued from this washing is carried out by heating, preferably by heating between 70 and 90° C., for example 80° C., between 30 min and 2 hours. If the temperature transfer liquid used in the platform is water the water retrieve during the washing of the roots is mixed with said temperature transfer liquid and together treated by heating as mentioned above.

Preferably, the methods of the invention, after recovering of the roots, preferably comprise various steps of decontamination:
the elements of the platform (lid, contained, temperature controlled system, pots . . . ) are decontaminate as mentioned above; and/or
the heat transfer liquid, and optionally the water recovering from the washing of the roots, are heated as described above;
the substrate and optionally the operator's clothing are decontaminate for example with autoclave.

In a specific embodiment the soil parasite is Orobanche. Preferably in this case the plant is sunflower or rapeseed. Thus the invention relates to a method of identification of plant, especially sunflower or rapeseed, resistance or tolerance to *Orobanche* comprising the steps of:
Sowing a seed of said plant on a substrate containing a standard quantity of *Orobanche* in at least one pot of a phenotyping platform according to the invention;
Cultivating the plant;
Recovering the roots of the plant after a predetermined duration of culture which depends on the development cycle of the *Orobanche* (typically 5 weeks);
Counting the number of nodules created by the parasite on the plant roots;
Determining whether the plant is resistant or tolerant to the parasite.

If the number of nodules per root is 0, the plant is resistant to *Orobanche*. If the number of nodules per root is significatively different and inferior to the number of nodule obtained for the susceptible plant, the plant is tolerant to *Orobanche*.

Preferably, this method can further comprise a step of recovering DNA and/or RNA of *Orobanche* for genotyping.

The present invention also relates to a method of identification of soil parasite population aggressiveness to a plant comprising the steps of:
Sowing a seed of said plant on a substrate containing different quantity of soil parasite from different origin, in at least one pot of the phenotyping platform according to the invention;
Cultivating the plant;
Recovering the plants after a predetermined duration of culture which depend on the soil parasite development cycle;
Note the roots and/or aerial damage of the plant.

In a specific embodiment the soil parasite is *Orobanche*. Preferably in this case the plant is sunflower or rapeseed. Thus the invention relates to a method of identification of pathogen population aggressiveness to a plant comprising the steps of:
Sowing sunflower seeds or rapeseed on a substrate containing different quantity of *orobanche* from different origin, in different pots of a phenotyping platform according to the invention;
Cultivating the plant;
Recovering the plants after a predetermined duration of culture which depends on the development cycle of the *Orobanche* (typically 5 weeks);
Counting the number of nodules created by the parasite on the plant roots;
Determining whether the plant is resistant or tolerant to the parasite.

Preferably, this method can further comprise the step of recovering DNA and/or RNA of *Orobanche* for genotyping.

The method of the invention is advantageously carried out in greenhouses comprising at least one platform according to the invention. The use of greenhouse is environmental friendly compared to growth chamber that can be used in other methods and enables to screen a great numbers of plants and soil parasites. It is thus for example possible to screen 1600 plants at the same time.

The method and the platform, of the invention, capacity can easily be compared to field capacity but with the critical advantage of having efficient and homogeneous infection.

The platform and the method of the invention are good predictive tools for field trial and can be used as screening platform to identify the more interesting plants or races of plant before going to field.

In the method according to the invention, the soil parasite is inserted into the substrate near the root before or after sowing of the seeds of the plant or at different stage of the seedling development.

The platform and the method of the invention enable to obtain results at an early stage of plant development and thus to retrieve rapid results without great expenses.

The scoring at roots level allows the breakthrough of the infection for *Orobanche* process in 3 major steps:
First development of the soil parasite (for example germination of *Orobanche*);
Attachment
Post-attachment.

It is thus possible to identify different resistance mechanism and traits to be stacked in the same genotype in order to enhance sustainable resistance.

Accordingly, the methods of the invention also comprises, after noting the roots and/or aerial damage of the plant, the recovery of DNA and/or RNA of the plants which have shown low interaction to the soil parasite for genotyping and the selection of the plants for the further steps of breeding.

The platform of the invention can also be used for testing plant tolerance to abiotic stress. For example, it can be used to consider heat stress and/or water deprivation but also cold test. Cold stress can also be used to determine the quality of seed lots before commercialization (quality control). It is also possible to retrieve DNA and/or RNA of the resistant plant for genotyping.

The invention also relates to a method to determine the race of a soil parasite comprising the steps of:
Implementing the method of determination of the interaction of different plants with different soil parasite as defined above;
Placing in each pot of a platform according to the invention a soil parasite and different plants for which the interaction with different soil parasite are known from the previous step;
Observing the plants which resist and determining the race of the soil parasite placed in the pot.

Preferably, this method can further comprise the step of recovering DNA and/or RNA of soil parasite (especially *Orobanche*) for genotyping.

The invention also relates to a method of identification of plant resistance or tolerance to drought comprising the steps of:
Sowing a seed plant on a substrate with a standard moisture in at least one pot of a phenotyping platform according to the invention
Cultivating the plant, according controlled drought condition
Recovering the plants after a predetermined duration of culture
Note the roots growth and architecture on the plant.

Control of drought can be done by the use of dispositive to control soil moisture. For examples capacitance probes are randomly positioned on the platform, and joined to irrigation means to trigger controlled irrigation when the moisture down under a predetermined value. Phenotyping of the roots can be done at the end of the culture by measure of root length, diameter or branching, software to do such measurement by image analysis are available.

BRIEF DESCRIPTION OF THE DRAWINGS

The invention will better be defined based on the following drawings.

EXAMPLES OF THE INVENTION

Figure 1:
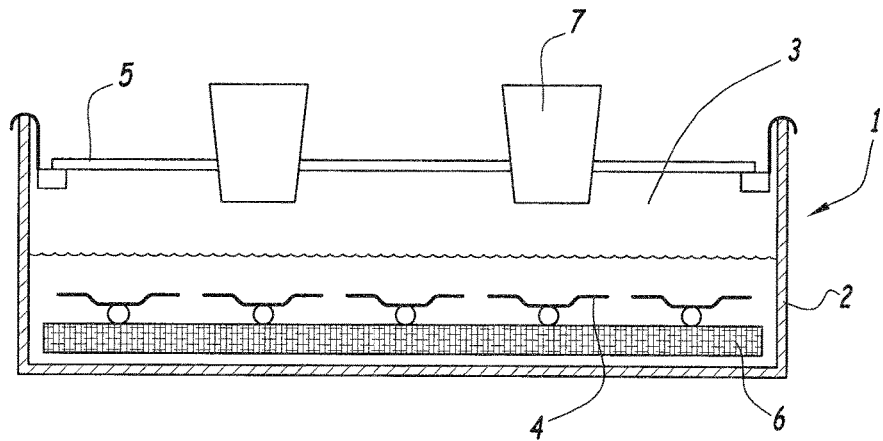
FIG. 1: represents a platform (1) according to the invention comprising a container (2) hermetically closed by a lid (5) comprising two pots (7) and delimiting an internal space (3) into which are place an insulating mean (6) and temperature control means (4) immersed in a temperature transfer liquid.
Figure 2:
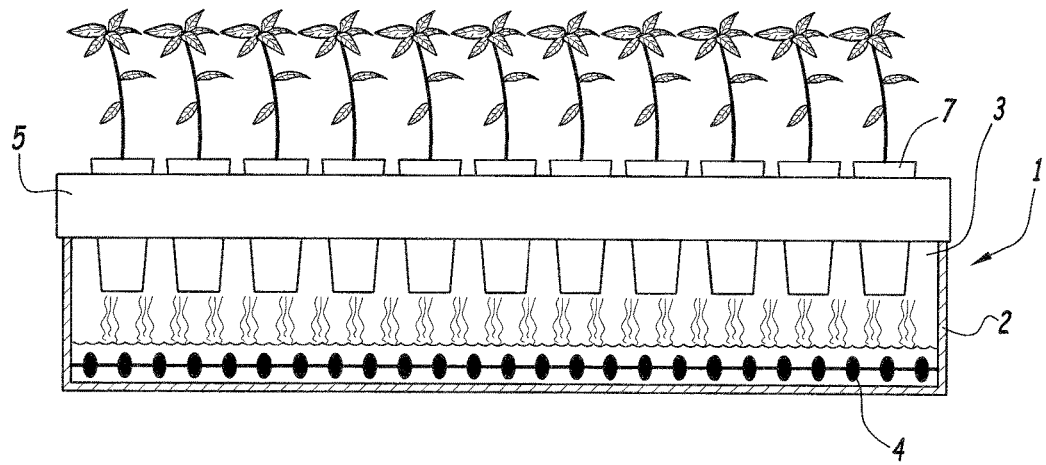
FIG. 2: represents a platform (1) according to the invention comprising a container (2) hermetically closed by a lid (5) comprising eleven pots (7) and delimiting an internal space (3) into which are place temperature control means (4) immersed in a temperature transfer liquid.
Figure 3:
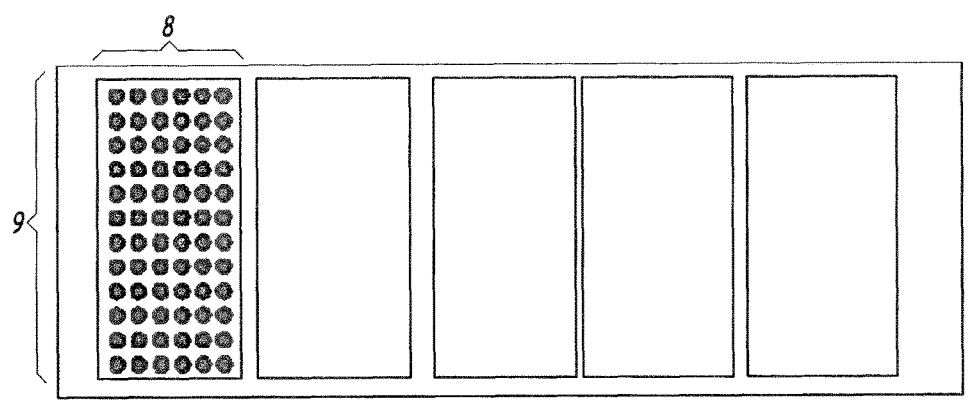
FIG. 3: represents an assembly of 5 platforms (I to V) according to the invention, each platform comprising 72 orifices (12 lines (9) (1 to 12) and 6 columns (8) (A to F)).
Figure 4:
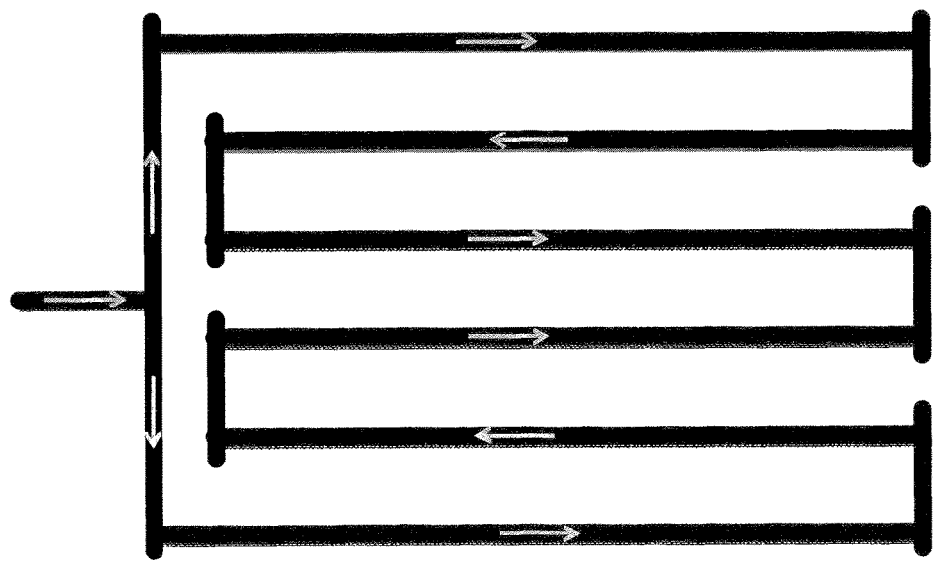
FIG. 4: represents an irrigation system according to the invention, the arrows representing the flow of water.

The below tests were carried out in a greenhouse comprises a platform composed of an aluminum container (2500×800×200 mm) and a lid (thickness 6 mm) composed of a polyethylene sheet of 5.6 mm thick covered in its two faces with an aluminum sheet of 0.21 mm.

The lid enables to hermetically close the container and is maintained thanks to spacer riveted. The lid comprises 360 orifices of diameter 4.5 or 5.5 cm (12 lines of 30 orifices) and pots. The pots have a diameter of 4.5 or 5.5 cm to fit the orifice's diameter and are 11 cm length.

The pots present are perforated and a cotton balls is placed in the hole. The pots are then filed with a substrate comprising blonde sphagnum peat and NPK fertilizer.

An aqua napping is placed at the bottom of the container. A heating cable (whose heating power is 300 W/m$^2$) is placed on the aqua napping and 4 cm of water (temperature transfer liquid) is added (the heating cable is totally immersed in water).

The 30 lines of orifices are irrigated by 5 independent irrigation unit, each irrigation unit is adapted to irrigate 6 lines.

Each pot can be identified by number of the irrigation unit 1 to 5, a letter A to E to address the position of the pot on the irrigation unit, and a range 1 to 12 to address the position of the plot on the table.

Example 1

Homogeneous and Controlled Temperature Around the Pot

The heating cable is set in order to have a temperature comprised between 27.5 and 28.5 in the container. After 14 hours of running the temperature was measured into the pots. The results are shown in the table below:

| I | A | B | C | D | E | F | II | A | B | C | D | E | F | III | A | B | C | D | E | F |
|---|---|---|---|---|---|---|---|---|---|---|---|---|---|---|---|---|---|---|---|---|
| 1 |   |   | 29 | 28.9 | 28.8 | 29 | 1 | 28.6 | 28.6 | 28.4 | 28.4 | 28.3 | 28.4 | 1 | 28.3 | 28.2 | 28 | 28.1 | 28.1 | 28.1 |
| 2 |   | 28.9 | 28.7 | 28.5 | 28.7 | 28.8 | 2 | 28.6 | 28.6 | 28.6 | 28.5 | 28.3 | 28.3 | 2 | 28 | 28 | 28.1 | 28.3 | 28.3 | 28.2 |
| 3 | 29 | 28.9 | 28.8 | 28.5 | 28.5 | 28.5 | 3 | 28.5 | 28.5 | 28.4 | 28.3 | 28.3 | 28.2 | 3 | 28 | 28.1 | 28.2 | 28 | 28 | 28.1 |
| 4 | 29 | 28.6 | 28.6 | 28.6 | 28.6 | 28.6 | 4 | 28.6 | 28.6 | 28.3 | 28.3 | 27.8 | 28.1 | 4 | 27.8 | 28 | 28 | 28.1 | 28.1 | 28.2 |

-continued

| | | | | | | | | | | | | | | | | | | | | |
|---|---|---|---|---|---|---|---|---|---|---|---|---|---|---|---|---|---|---|---|---|
| 5 | 29 | 28.9 | 28.7 | 28.7 | 28.6 | 28.7 | 5 | 28.4 | 28.4 | 28.3 | 28 | 27.9 | 28 | 5 | 28 | 28 | 27.9 | 27.9 | 28 | 28 |
| 6 | 29 | 28.8 | 28.7 | 28.5 | 28.6 | 28.5 | 6 | 28.6 | 28.5 | 28.3 | 28 | 28 | 27.8 | 6 | 27.8 | 27.5 | 27.7 | 27.7 | 27.7 | 27.8 |
| 7 | | 29 | 28.8 | 28.7 | 28.5 | 28.5 | 7 | 28.4 | 28.2 | 28 | 28 | 27.9 | 27.7 | 7 | 27.8 | 27.8 | 27.7 | 27.6 | 27.7 | 27.8 |
| 8 | 29 | 28.8 | 28.6 | 28.6 | 28.6 | 28.5 | 8 | 28.6 | 28.4 | 28.3 | 28 | 27.7 | 27.7 | 8 | 27.5 | 27.6 | 27.6 | 27.6 | 27.6 | 27.5 |
| 9 | 29 | 29 | 28.8 | 28.8 | 28.6 | 28.5 | 9 | 28.6 | 28.6 | 28 | 27.9 | 27.5 | 27.6 | 9 | 27.5 | 27.5 | 27.4 | 27.4 | 27.5 | 27.5 |
| 10 | 29 | 28.8 | 28.7 | 28.5 | 28.3 | 28.4 | 10 | 28.3 | 28.2 | 28.1 | 28.9 | 27.7 | 27.5 | 10 | 27.2 | 27.3 | 27.2 | 27.4 | 27.4 | 27.5 |
| 11 | 29 | 29 | 28.9 | 28.8 | 28.5 | 28.4 | 11 | 28.1 | 27.9 | 27.7 | 27.6 | 27.5 | 27.5 | 11 | 27.4 | 27.2 | 27.1 | 27.1 | 27.1 | 27 |
| 12 | 28.7 | 28.8 | 28.5 | 28.3 | 28.3 | 28.4 | 12 | 28.1 | 28.2 | 28.1 | 28 | 27.7 | 27.6 | 12 | 27.2 | 27 | 27 | 27.4 | 27.4 | 27.4 |

| IV | A | B | C | D | E | F | V | A | B | C | D | E | F |
|---|---|---|---|---|---|---|---|---|---|---|---|---|---|
| 1 | 28.1 | 28.1 | 28 | 27.9 | 28 | 27.9 | 1 | 28 | 28.1 | 28 | 28 | 28 | 28 |
| 2 | 28.1 | 28.2 | 28.2 | 28.1 | 28.1 | 28 | 2 | 28.2 | 28.2 | 28.1 | 27.9 | 28.1 | 27.9 |
| 3 | 28.3 | 28.2 | 28.2 | 28.2 | 28.2 | 28.3 | 3 | 28.2 | 28.1 | 28.2 | 28.2 | 28.2 | 28.1 |
| 4 | 28 | 28.1 | 28 | 28.2 | 28.2 | 28.2 | 4 | 28.3 | 28.3 | 28.3 | 28.2 | 28.9 | 28.1 |
| 5 | 28.1 | 28.1 | 28.1 | 28.1 | 28.2 | 28.2 | 5 | 28.3 | 28.4 | 28.4 | 28.4 | 28.4 | 28.4 |
| 6 | 27.6 | 27.9 | 28 | 28 | 28 | 28.2 | 6 | 28.4 | 28.4 | 28.5 | 28.6 | 28.6 | 28.5 |
| 7 | 27.9 | 27.9 | 28 | 28.1 | 28.2 | 28.1 | 7 | 28.4 | 28.4 | 28.4 | 28.2 | 28.5 | 28.5 |
| 8 | 27.7 | 27.7 | 27.6 | 27.8 | 27.8 | 28 | 8 | 28.2 | 28.2 | 28.3 | 28.3 | 28.4 | 28.4 |
| 9 | 27.6 | 27.9 | 27.6 | 27.7 | 28 | 27.9 | 9 | 28.2 | 28.3 | 28.3 | 28.4 | 28.4 | 28.5 |
| 10 | 27.3 | 27.4 | 27.4 | 27.4 | 27.5 | 27.6 | 10 | 27.9 | 28 | 28.1 | 28.1 | 28.2 | 28.3 |
| 11 | 27.1 | 27.2 | 27.3 | 27.4 | 27.6 | 27.6 | 11 | 28.2 | 28.3 | 28.4 | 28.4 | 28.4 | 28.4 |
| 12 | 27.4 | 27.5 | 27.5 | 27.5 | 27.5 | 27.5 | 12 | 27.6 | 27.8 | 28 | 28 | 28.2 | 28.1 |

The temperatures varied between 27 and 29.5. The temperature is considered homogeneous. This example clearly shows that the platform according to the invention enables to have controlled and homogeneous temperature conditions around each pot.

Example 2

Determination of Resistance or Tolerance of Sunflower Races to Orobanche

The greenhouse and the 360 pots platform disclosed above are used. The pots not used are hermetically closed.

Figure 5:
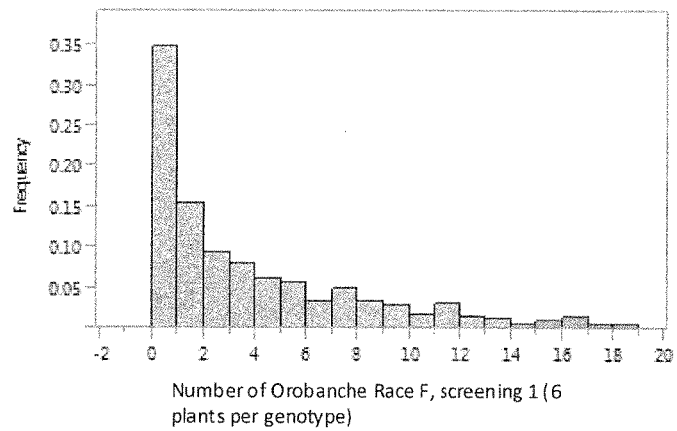
FIGS. 5 to 7: represents respectively the distribution (histograms) of the frequency of data obtained with the method of the invention for sunflower and orobanche race F (two screening (FIGS. 5 and 6) and field data (FIG. 7).
Figure 6:
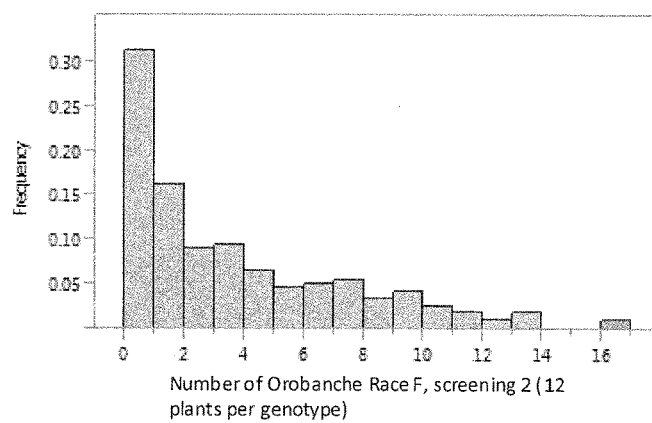

An equal quantity of Orobanche seeds of race F (Spain) are placed in each pot with a seed of sunflower. 300 different sunflower genotype are placed on the platform and studied, six to twelve repeats are studied by genotype and this experiment has been done twice (screening 1 and 2 respectively FIGS. 5 and 6).

The heating cable is set in order to have a temperature comprised between 27.5 and 28.5 in the container. The temperature inside the pots is checked once a week and is regulated thanks to a thermostat if needed.

The platform is located in a greenhouse where plants are cultivated under Sodium vapor lights (400 W), at a temperature of 18 to 22° C. and a hygrometry comprised between 40 and 60%. The pots are watered once a week during 50 seconds with a drop wise irrigation system.

Five weeks after sowing the heating cable, the irrigation system and the lights are shut down. The roots of each plant are carefully washed in separate container comprising water. The numbers of nodules on the roots are count.

The results are shown on the histograms of FIGS. 5 and 6. The frequency distribution of results of the first and second screening is shown in FIGS. 5 and 6 respectively. The average numbers of nodules per plants for one genotype varied between 0 and 20 and are represented by the histogram (axe x) for each line of sunflower, the axe y represents the frequency of sunflower genotypes having the considered average number of nodules.

Figure 8:
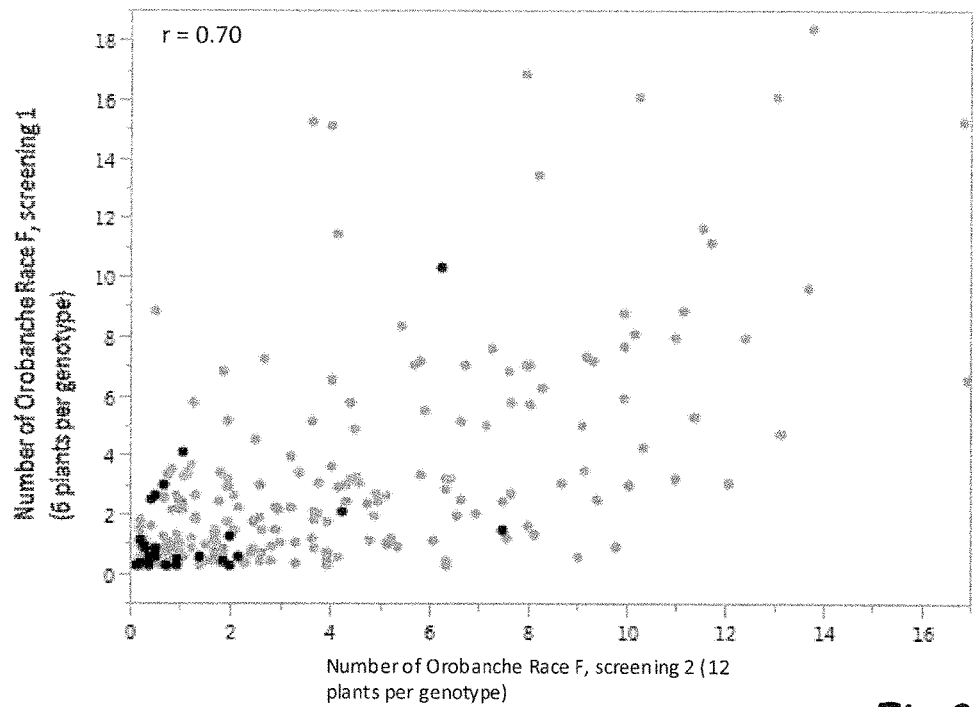
FIGS. 8 to 10: represents respectively the correlation (scatter plots with pearson r value) of the results obtained in screening 1 and 2 (FIG. 8), of the results obtained in screening 1 and field (FIG. 9) and of the results obtained in screening 2 and field (FIG. 10).

The comparison of results from screening 1 and 2 are shown in FIG. 8. Each genotype studied in this experiment corresponds to a point. The projection of the point in the Y-axis gives the number of nodules obtained for the first screening and the projection of the point in the X-axis gives the number of nodules obtained for the second screening.

This graph allows calculating the Pearson correlation coefficient with the following formula:

$$r = \frac{\sigma_{xy}}{\sigma_x \sigma_y}$$

$\sigma_{xy}$ is the covariance between variable x and y
$\sigma_x$ is the standard deviation of variable x
$\sigma_y$ is the standard deviation of variable y The Pearson correlation coefficient calculated between screening 1 and screening 2 is 0.7. The results show what, the method of the invention and the use of the platform according to the invention are repeatable.

Example 3

Correlation between Data Obtained in Fields

The correlation used the data obtained from the two screening of example 2. The same 300 sunflower genotypes were phenotyped in field in order to address the reliability of the test and its ability to predict field behavior. One line per genotype with around 20 plants was sown in Spain field, supposed to contain Orobanche seeds form race F. At ad hoc plant stage, the number of plants with at least 1 emerged Orobanche is scored per line. Based on this scoring the percentage of plants on the line with at least on emerged Orobanche is computed.

Figure 7:
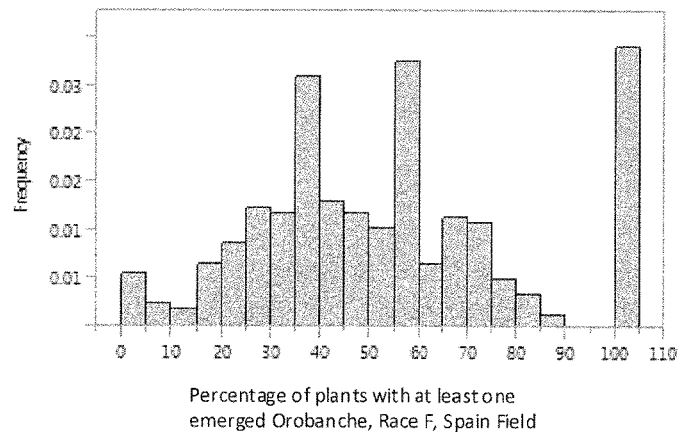

FIG. 7 gives the frequency distribution of the percentage of plants with at least on emerged Orobanche per sunflower genotype based on Spain field experiment.

Figure 9:
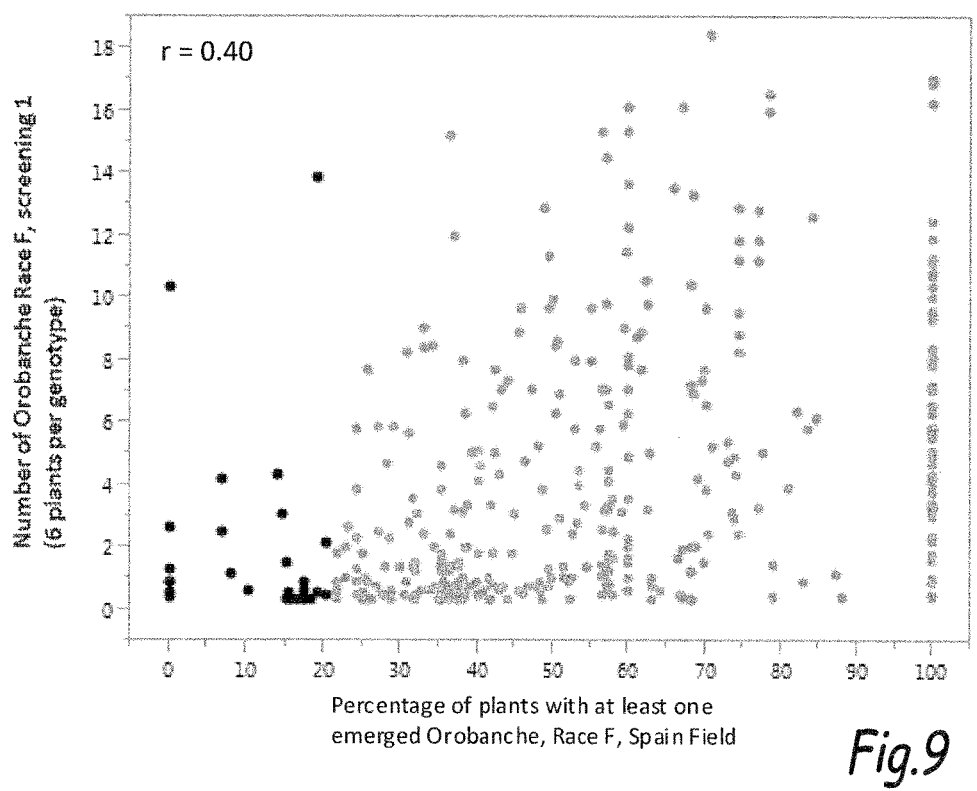
Figure 10:
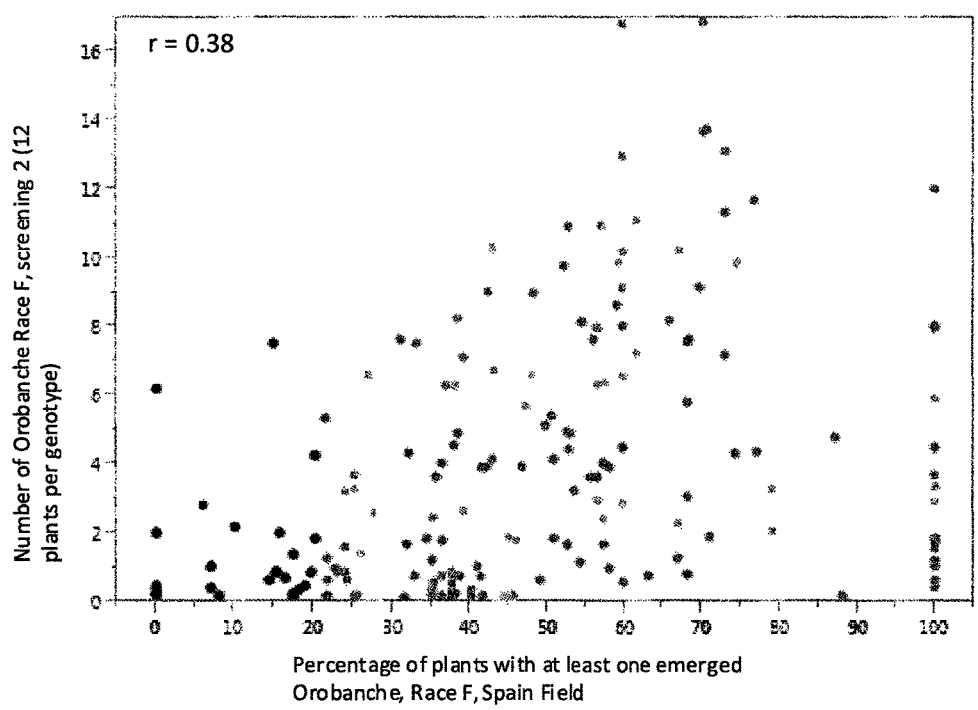

FIGS. 9 and 10 display the correlation between respectively screening 1 and 2 and field scoring, produced for 300 sunflower genotypes with Orobanche seeds from race F (Spain origin), according to the present invention and data set obtain in field on the same set of sunflower genotype in Spain, known to contain race F Orobanche seeds.

The comparison of results from screening 1 and the field scoring and from screening 2 and the field scoring are shown respectively in FIGS. 9 and 10. Each genotype is represented by a point. The projection of the point in the Y-axis gives the number of average nodules per plant tested during the first or second screening (respectively FIGS. 9 and 10 and the projection of the point in the X-axis gives the percentage of plants with at least one emerged *orobanche* during the field screening).

These graphs allow calculating the Pearson correlation coefficient which is from 0.41 for the first screening and 0.38 for the second screening.

Therefore, the method of the invention has been demonstrated to be an accurate predictive tool for field trial (r=0.4), and can be used a prescreening tool in breeding program. The results show that the use of the platform according to the invention enables to determine the resistance or tolerance to a plant with respect of a soil parasite.

Example 4

Destruction of Trash and Cleaning of the Platform

Water contained in the container (water initially added in the container and water evacuated by the pots (evacuation of excessive amount of water caused by the irrigation by the hole in the bottom of each pot) and water resulting from the washing of the platform are heated at 80° C. during one hour in order to eliminate *Orobanche* and sunflower seeds.

The solid trash (especially the plants and the substrate) are placed in autoclavable bag comprising two layers. The autoclavable bag is placed in another autoclavable bag and then put into a dump to which a vapor generator is connected. The vapor generator is switched. After treatment the resulting trash are disposed of with household waste.

The elements of the platform (container, lid, heating material) are washed by soaking in Javel water.

The invention claimed is:

1. A plant biotic agent phenotyping platform comprising a container hermetically sealed with a lid delimiting an internal space divided into two spaces:
   a lower internal space which comprises at least one thermostat immersed in a temperature transfer liquid; and
   an upper internal space, the surface of the temperature transfer liquid being the border between the lower internal space and the upper internal space;
the lid comprising at least one orifice which is adapted to fit a pot and at least one pot whose bottom part is contained in the upper internal space and which is adapted to receive plant seed and soil parasites, and to enable growth of the plant and development of such soil parasites,
   wherein the pot has such a size that when it is placed within the orifice, the pot is not in contact with the temperature transfer liquid;
   wherein the pot comprises a plant seed sowed on a substrate;
   wherein the pot further comprises at least one soil parasite; and
   wherein the platform is configured to determine a resistance or a tolerance between the plant and the soil parasite.

2. The plant biotic agent phenotyping platform of claim 1, further comprising a decontaminator.

3. The plant biotic agent phenotyping platform of claim 2, wherein the decontaminator further comprises a chlorinated water.

4. The plant biotic agent phenotyping platform according to claim 1 further comprising a drip system delivering a controlled and equal amount of water independently to each pots.

5. The plant biotic agent phenotyping platform according to claim 1, wherein the soil parasite is broomrape and the plant is sunflower or rapeseed.

6. The plant biotic agent phenotyping platform according to claim 1, wherein the temperature transfer liquid is water.

7. The plant biotic agent phenotyping platform according to claim 1, wherein the container also comprises an insulating material.

8. The plant biotic agent phenotyping platform according to claim 1, wherein the container is 1 to 3 m of length and 50 cm to 1 m of width.

9. The plant biotic agent phenotyping platform according to claim 1, comprising from 50 to 500 orifices and pots.

10. A kit comprising the phenotyping platform according to claim 1, and further comprising at least one element selected from the group consisting of an irrigator, pot lighting, and a decontaminator.

11. A phenotyping greenhouse comprising at least one phenotyping platform according to claim 1, further comprising at least one element selected from the group consisting of an irrigator, pot lighting, and a decontaminator and/or a thermostat for controlling temperature and/or an instrument for controlling hygrometry of the greenhouse.

12. A method of identification of plant resistance or tolerance to a root parasite or interaction with a symbiotic organism comprising:
   sowing a seed plant on a substrate containing a standard quantity of soil parasite in at least one pot of a phenotyping platform, wherein the phenotyping platform is the phenotyping platform according to claim 1:
   cultivating the plant;
   recovering the plants after a predetermined duration of culture; and
   noting the roots and/or aerial damage on the plant.

13. The method according to claim 12 for the identification of plant resistance or tolerance to an Orobanche parasite comprising:
   sowing the seed of the plant on a substrate containing a standard quantity of Orobanche in at least one pot of the phenotyping platform of claim 1,
   cultivating the plant;
   recovering the roots of the plant;
   counting the number of nodules created by the parasite on the plant roots; and
   determining whether the plant is resistant or tolerant to the Orobanche parasite.

14. The method according to claim 13 further comprising the recovery of DNA and/or RNA of Orobanche for genotyping.

15. The method according to claim 12 further comprising the genotyping of the plants having shown resistance or higher tolerance and the use of this plant for breeding new varieties.

16. A method of identification of soil parasite population aggressiveness to a plant comprising:
   sowing seeds plant on a substrate containing different quantity of soil parasite from different origin in at least one pot of a phenotyping platform according to claim 1;
   cultivating the plant;
   recovering the plants after a predetermined duration of culture; and
   noting the roots and/or aerial damage on the plant.

17. The method according to claim 16 for the identification of Orobanche population aggressiveness to a plant comprising:
    sowing Orobanche plants or seeds plants on a substrate containing a standard quantity in at least one pot of the phenotyping platform of claim 1,
    cultivating the plant;
    recovering the roots of the plant;
    counting the number of nodules created by the parasite on the plant roots; and
    determining whether the Orobanche is aggressive to the plant.

18. A method of identification of plant resistance or tolerance to drought comprising:
    sowing a seed plant on a substrate with a standard moisture in at least one pot of a phenotyping platform comprising:
        a container hermetically sealed with a lid delimiting an internal space divided into two spaces,
            a lower internal space which comprises at least one thermostat immersed in a temperature transfer liquid; and
            an upper internal space, the surface of the temperature transfer liquid being the border between the lower internal space and the upper internal space;
        the lid comprising at least one orifice which is adapted to fit a pot and at least one pot whose bottom part is contained in the upper internal space and which is adapted to receive plant seed and to enable growth of the plant; wherein the pot has such a size that when it is placed within the orifice, the pot is not in contact with the temperature transfer liquid; wherein the pot comprises a plant seed sowed on a substrate; and wherein the platform is configured to determine the resistance or tolerance to drought;
    cultivating the plant, according to controlled drought condition;
    recovering the plants after a predetermined duration of culture; and
    noting the roots growth and architecture on the plant.

* * * * *